| United States Patent [19] | [11] | 4,217,416 |
|---|---|---|
| Daumy | [45] | Aug. 12, 1980 |

[54] BIOTRANSFORMATION PREPARATION OF 2,3-DIHYDROXYBENZOIC ACID

[75] Inventor: Gaston O. Daumy, Gales Ferry, Conn.

[73] Assignee: Pfizer, Inc., New York, N.Y.

[21] Appl. No.: 31,626

[22] Filed: Apr. 19, 1979

[51] Int. Cl.$^2$ ................................................. C12P 7/42
[52] U.S. Cl. ..................................... 435/146; 435/874
[58] Field of Search ........................................... 435/146

[56] References Cited

U.S. PATENT DOCUMENTS

| 3,634,192 | 1/1972 | Brilland | 435/146 |
| 3,645,847 | 2/1972 | Eltz | 435/146 |

*Primary Examiner*—Alvin E. Tanenholtz
*Attorney, Agent, or Firm*—Connolly and Hutz

[57] ABSTRACT

The bioconversion of m-hydroxybenzoate to 2,3-dihydroxybenzoate in high yield is accomplished employing a mutant strain of *Pseudomonas testosteroni*.

3 Claims, No Drawings

BIOTRANSFORMATION PREPARATION OF 2,3-DIHYDROXYBENZOIC ACID

BACKGROUND OF THE INVENTION m-Hydroxybenzoate has been shown to serve as a growth substrate for a variety of microorganisms which hydroxylate this compound either at carbon 4 or 6 in preparation for ring cleavage as taught in J. Bacteriol. 107, 468–475 (1971); Dokl. Acad. Nauk SSR. 234, 696–698 (1977); Bull. Agr. Chem. Soc. Japan 24, 211–216 (1960); Ann. Inst. Pasteur, Paris 117, 47–57 (1969); Arch. Mikrobiol, 59, 302–314 (1967); and J. Gen. Appl. Microbiol. 4, 241–258 (1958). The enzymes which catalyze the hydroxylation of m-hydroxybenzoate to protocatechuate and gentisate have been purified from *Pseudomonas testosteroni*, Biochem. Biophys. Res. Commun. 55, 1102–1110 (1955), and *Pseudomonas aeruginosa*, Biochem. Biophys. Res. Commun. 55, 897–903 (1973), respectively.

Previously reported procedures for the bioconversion of m-hydroxybenzoate did not provide for the hydroxylation of this compound to form desired 2,3-dihydroxybenzoate which is also difficult to prepare by chemical synthesis. 2,3-Dihydroxybenzoate is a potentially useful iron-chelating drug as discussed in J. Pharmacol. Exp. Ther. 190 (3), 187–92 (1974) and Iron Metabolism. Thalassemia Conf. p. 187–192 (1975).

SUMMARY OF THE INVENTION

The present invention is concerned with a biotransformation process for preparing 2,3-dihydroxybenzoate in high yield from m-hydroxybenzoate employing a mutant strain of *Pseudomonas testosteroni*. This represents the first biochemical report of a 3-hydroxybenzoate-2-hydroxylase activity.

DETAILED DESCRIPTION OF THE INVENTION

Mutant cultures of *Pseudomonas testosteroni* strain 139 ATCC 17511 were generated by ultraviolet light irradiation and tested for their ability to convert m-hydroxybenzoate to 2,3-dihydroxybenzoate.

A desired mutant strain has been deposited in the American Type Culture Collection, Rockville, Md. under their accession number ATCC 31492. The permanency of the deposit of this culture at The American Type Culture Collection at Rockville, Maryland and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

Cells of *Pseudomonas testosteroni* ATCC 31492 are transferred to an appropriate aqueous nutrient medium, preferably Stanier's basal salts medium supplemented with 0.5% yeast extract. Cells grown overnight are harvested aseptically by centrifugation and washed in sterile basal salts solution. A suspension of these washed cells is placed in sterile flasks containing filter sterilized solutions of lactate and m-hydroxybenzoate. The ratio of cell mass (dry weight) to weight of m-hydroxybenzoate may range from about 2:1 to about 10:1 with 5:1 the preferred ratio. The concentration of m-hydroxybenzoate may vary from about 2 mM to about 10 mM with about 7 mM the preferred concentration. The bioconversion pH may range from 5 to 9 with neutrality preferred. Temperatures of 20° to 45° C. may be employed with 30° C. the preferred temperature. The bioconversion period is monitored by the amount of 2,3-dihydroxybenzoate produced as determined by high pressure liquid chromatography. Substantial bioconversion is obtained in about 3 to 10 hours. The bacterial cells are removed by centrifugation or filtration and 2,3-dihydroxybenzoate separated and purified by known methods.

Alternatively, the bioconversion may be carried out by contacting m-hydroxybenzoate with 3-hydroxybenzoate-2-hydroxylase isolated from *Pseudomonas testosteroni* ATCC 31492 cells by conventional enzyme technology.

Reverse phase high pressure liquid chromatography is carried out on a Waters Associates $\mu$ $C_{18}$ column (25 cm$\times$4 mm ID). The mobile phase is made up of 4 volumes of 50 mM acetic acid and 1 volume of methanol. The flow rate is kept constant at 1.2 ml/min. and the materials eluted from the column are detected by their UV absorbance at 280 nm.

The novel process of the present invention provides for the first time the bioconversion of m-hydroxybenzoate to desired 2,3-dihydroxybenzoate. The simple and facile process makes possible the commerical production of 2,3-dihydroxybenzoate and the development and exploitation of this potentially clinically useful and important product.

EXAMPLE 1

*Pseudomonas testosteroni* ATCC 31492 was grown in 4 liters of Stanier's basal salts medium supplemented with 0.5% yeast extract medium for 18 hours at 28° C. The cell mass obtained was incubated overnight at 30° C. in one liter of basal salts medium supplemented with 1 gram of m-hydroxybenzoate and 1 gram of lactate. The filtered spent broth was lyophilized and the solids dissolved in 100 ml of saturated brine. After adjustment to pH 2.5 with 6 N HCl, the aqueous solution was extracted with ethyl acetate (4$\times$50 ml), the organic layer dried over anhydrous magnesium sulfate and then evaporated in vacuo. The residue, after crystallization from water, afforded 470 mg of an off-white solid. The material was shown by high pressure liquid chromatography to be a mixture of 2,3-dihydroxybenzoic acid and m-hydroxybenzoic acid in a ratio of 89:11.

Three crystallizations from water yielded a crystalline compound which was homogeneous by high pressure liquid chromatography and identical in physical and spectral characteristics, melting point and mixed melting point with authentic 2,3-dihydroxybenzoic acid (Aldrich Chemical Co.).

EXAMPLE 2

The process of Example 1 may be repeated with comparable results by contacting m-hydroxybenzoate with 3-hydroxybenzoate-2-hydroxylase isolated from the cells of *Pseudomonas testosteroni* ATCC 31492.

EXAMPLE 3

The biotransformation of m-hydroxybenzoate to 2,3-dihydroxybenzoate as a function of m-dihydroxybenzoate concentration by *Pseudomonas testosteroni* ATCC 31492 is shown in the following table:

| [MHB]$_0$ (mM) | [MHB]$_{18\ hrs}$ (mM) | [2,3-DHB]$_{18\ hrs}$ (mM) | % Yield (based on consumed MHB) |
|---|---|---|---|
| 0 | 0 | 0 | 0 |
| 1.8 | 0 | 1.0 | 55.6 |
| 3.7 | 0.44 | 1.6 | 49.1 |
| 7.3 | 1.55 | 2.9 | 50.4 |

EXAMPLE 4

The biotransformation of m-hydroxybenzoate to 2,3-dihydroxybenzoate by *Pseudomonas testosteroni* ATCC 31492 as a function of time is shown in the following table:

| Time (hrs) | 2,3-DHB (mM) |
|---|---|
| 0 | 0 |
| 3 | 2.0 |
| 5.5 | 2.7 |
| 6.5 | 3.25 |

I claim:
1. A process for preparing 2,3-dihydroxybenzoate which comprises contacting m-hydroxybenzoate with the cells of *Pseudomonas testosteroni* ATCC 31492 or 3-hydroxybenzoate-2-hydroxylase obtained therefrom at a pH of 5 to 9 and a temperature of 20° to 45° C. until the bioconversion is substantially complete.
2. The process of claim 1 wherein said pH is 6.8 to 7.2.
3. The process of claim 1 wherein said temperature is 28°–30° C.

* * * * *